United States Patent [19]

Lisowsky

[11] Patent Number: 5,523,435
[45] Date of Patent: Jun. 4, 1996

[54] PROCESS FOR THE SYNTHESIS OF MONOMETHYLMETALLOCENES AND DIMETHYLMETALLOCENES AND THEIR SOLUTIONS SPECIFICALLY FOR USE IN THE POLYMERIZATION OF OLEFINS

[75] Inventor: Richard Lisowsky, Kamen, Germany

[73] Assignee: Witco GmbH, Bergkamen, Germany

[21] Appl. No.: 429,526

[22] Filed: Apr. 26, 1995

[30] Foreign Application Priority Data

May 13, 1994 [DE] Germany .......................... 44 16 894.2

[51] Int. Cl.$^6$ .............. C07F 17/00; C07F 7/00; C07F 5/00
[52] U.S. Cl. ................. 556/11; 556/12; 556/28; 556/53; 534/15
[58] Field of Search ................. 556/11, 12, 28, 556/53; 534/15

[56] References Cited

U.S. PATENT DOCUMENTS

5,330,948  7/1994  Marks et al. .................... 502/104

FOREIGN PATENT DOCUMENTS

| | | |
|---|---|---|
| 0468537A1 | 1/1988 | European Pat. Off. |
| 0302424A1 | 7/1988 | European Pat. Off. |
| 0416815A2 | 8/1990 | European Pat. Off. |
| 0420436A1 | 9/1990 | European Pat. Off. |
| 0519237A2 | 5/1992 | European Pat. Off. |
| 0522581A1 | 7/1992 | European Pat. Off. |
| 0549900A1 | 11/1992 | European Pat. Off. |
| 0576970A1 | 6/1993 | European Pat. Off. |
| 858540 | 1/1961 | United Kingdom. |

OTHER PUBLICATIONS

Base–Free Cationic 14–Electron Alkyls of Ti, Zr and Hf as Polymerisation Catalysts; A Comparison; Journal of Organometallic Chemistry, 434 (1992) C1–C5; M. Bochmann and S. J. Lancaster.

Lewis–Base–Free Cationic Zirconocene Complexes Containing and Alkenyl Ligand; Organometallics (1991), 10; pp. 3910–3918; A. D. Horton and A. G. Orpen.

Ionic, Base–Free Zirconocene Catalysts For Ethylene Polymerization; J. Am. Chem. Soc. (1989), 111; pfs 2728–2729; G. G. Hlatky, H. W. Turner and R. R. Eckman.

"Organometallic Chemistry of Titanium, Zirconium and Hafnium," P. C. Wailes, R. S. P. Couttes and H. Weigold, 1974, Academic Press, Inc., 92–97, 150–151, 185–187.

Gmelins Handbook of Inorganic Chemistry, vol. 10, Organo–Zirconium Compounds, 1973, Verlag Chemie–Weinheim/Bergstrasse, pp. 54–58.

"Chemistry of Organo–Zirconium and—Hafnium Compounds," D. J. Cardin, M. F. Lappert, C. L. Raston, 1986, Ellis Horwood Limited 145–180.

*Primary Examiner*—Porfirio Nazario-Gonzales
*Attorney, Agent, or Firm*—Scully, Scott, Murphy & Presser

[57] ABSTRACT

Disclosed is a process for preparing methyltransition metal compounds in which the halide metallocene precursor to be alkylated is initially charged in a hydrocarbon desired for the subsequent application, admixed with an aluminum alkyl and subsequently converted by addition of an inorganic salt into the end product:

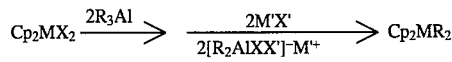

The reaction solution thus obtained can be freed of precipitated salts by simple filtration and directly used for polymerization, since the dialkylmetallocene is obtained in high purity and yield. If desired, it can also be isolated without problems.

7 Claims, No Drawings

PROCESS FOR THE SYNTHESIS OF MONOMETHYLMETALLOCENES AND DIMETHYLMETALLOCENES AND THEIR SOLUTIONS SPECIFICALLY FOR USE IN THE POLYMERIZATION OF OLEFINS

BACKGROUND OF THE INVENTION

The present invention relates to an improved process for preparing alkyl-transition metal complexes in particular monoalkylmetallocenes and dialkylmetallocenes, and to a process for preparing solutions of such compounds which are directly suitable for use in the polymerization of olefins.

Monoalkylmetallocene and particularly dialkylmetallocene compounds can in combination with specific cocatalysts, such as, for example, aluminoxanes or, in particular, triphenylboron derivatives, tetraphenylborate derivatives and alkylaluminum fluorides, form highly active catalyst systems (J. Organomet. Chem. 1992, 434.C1–C5, Organometallics 1991, 10, 3910; J. Am. Chem. Soc. 1989, 111, 2728; EP-A-O 522 581; EP-A-0 468 537).

Processes hitherto known in the literature for preparing monoalkylmetallocene and dialkylmetallocene compounds (in particular dimethyl compounds) in which lithium alkyls or alkyl Grignard compounds are used, have a series of disadvantages.

As a result of the use of methyl Grignard or methyllithium, the syntheses are tied to polar solvents such as, typically, diethyl ether or tetrahydrofuran. However, these solvents are catalyst poisons for the application in olefin polymerization, so that after the reaction of the metallocenes with the corresponding alkylating agent, the solvent has to be completely removed and the compound has to be isolated in pure form.

Furthermore, depending on the metallocene, the yields in their reactions to give the corresponding alkyl derivatives are very variable. (Chemistry of Organo-Zirconium and -Hafnium Compounds", D. J. Cardin, M. F. Lappert, C. L. Raston, 1986, Ellis Horwood Limited, 145–180; "Organometallic Chemistry of Titanium, Zirconium and Hafnium", P. C. Wailes, R. S. P. Coutts and H. Wiegold, 1974, Academic Press, Inc., 92–97, 150–151, 185–187; Gmelins Handbook of Inorganic Chemistry, Volume 10, Organo-Zirconium Compounds, 1973, Verlag Chemie—Weinheim/Bergstrasse, p. 54–58; Gmelins Handbook of Inorganic Chemistry, Volume 11, Organo-Hafnium Compounds, 1973, Verlag Chemie—Weinheim/Bergstrasse, p. 12).

It is therefore an object of the present invention to develop a process which overcomes these disadvantages of the prior art and by means of which the pure alkyl-transition metal compounds either can be prepared directly in high yields or even can be obtained without additional work-up steps directly in the solutions of the alkyl-transition metal compounds which are free of catalyst poisons and can be used in olefin polymerization.

BRIEF SUMMARY OF THE INVENTION

This object is achieved by reaction of halogen-transition metal compounds with aluminum alkyls and inorganic salts in hydrocarbons according to the general scheme:

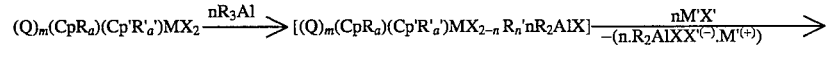

which in a particular embodiment conforms to the scheme:

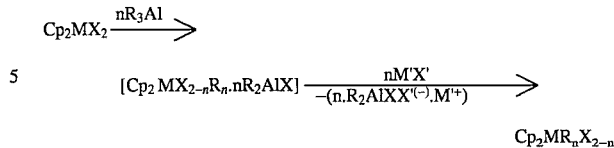

wherein n is 1 or 2, and the other symbols are as defined herein.

DETAILED DESCRIPTION OF THE INVENTION

The invention accordingly provides a process for preparing compounds of the general formula (1)

$$(Q)_m(CpR_a)(Cp'R'_{a'})M(CH_3)_nX_{2-n} \qquad (1)$$

where
- Cp is a cyclopentadienyl, an indenyl, or a fluorenyl radical;
- R and R' are independently alkyl, alkoxy, alkylamino, dialkylamino, alkoxyalkyl, aryl-alkyl, aryloxy-alkyl, or phosphine; $0 \leq a \leq 5$ and $0 \leq a' \leq 5$;
- Cp' is one of the groups Cp, or when a' is 1, Cp'R' can be NR' wherein R' is an alkyl or aryl radical; and
- Q is a single-membered or multi-membered bridge

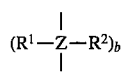

between Cp and Cp', where $R^1$ and $R^2$ are identical or different and are a hydrogen atom, a $C_1$–$C_{10}$-alkyl group or a $C_6$–$C_{10}$-aryl group, Z is carbon, silicon or germanium and b is 1, 2 or 3;
- M is a transition metal of the groups III to VI of the Periodic Table, in particular Ti, Zr or Hf;
- X is halogen, in particular Cl or Br;
- can be 1 or 2;
- can be 0 or 1.

The halogen-transition metal compounds used according to the invention correspond to the general formula (2)

$$(Q)_m(CpR_a)(Cp'R'_{a'})MX_2 \qquad (2)$$

where
- Cp is a cyclopentadienyl, an indenyl or a fluorenyl radical;
- R and R' are independently alkyl, alkoxy, alkylamino, dialkylamino, alkoxyalkyl, aryl-alkyl, aryloxy-alkyl or phosphine; $0 \leq a \leq 5$ and $0 \leq a' \leq 5$;
- Cp' is one of the groups Cp or when a' is 1, Cp'R' can be NR' wherein R' is an alkyl or aryl radical; and

Q is a single-membered or multi-membered bridge

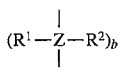

between Cp and Cp', where $R^1$ and $R^2$ are identical or different and are a hydrogen atom, a $C_1$–$C_{10}$-alkyl group or a $C_6$–$C_{10}$-aryl group, Z is carbon, silicon or germanium, and b is 1, 2 or 3;

M is a transition metal of the groups III to VI, in particular Ti, Zr or Hf;

X is halogen, in particular Cl or Br; and m can be 0 or 1.

Referring to the R and R' substituents, each one can be alkyl containing 1 to 10 carbon atoms, for example methyl (including dimethyl and trimethyl);

alkoxy containing 1 to 10 carbon atoms, for example methoxy (including dimethoxy and trimethoxy);

alkylamino and/or dialkylamino, wherein each alkyl group contains 1 to 10 carbon atoms, for example dimethylamino and dipropylamino (including bis(dimethylamino));

alkoxyalkyl containing a total of 2 to 20 carbon atoms;

aryl-alkyl and/or aryloxy-alkyl groups wherein the aryl group contains 6 to 10 carbon atoms and the alkyl portion contains 1 to 10 carbon atoms;

phosphine, including phosphine substituted with 1 or 2 groups each of which is $C_1$–$C_{10}$ alkyl or $C_6$–$C_{10}$ aryl, for example diphenylphosphino.

These compounds belong to the known prior art and are described, for example, in "Chemistry of Organo-Zirconium and -Hafnium Compounds" D. J. Cordin; M. F. Lappert; C. L. Raston, 1986, Ellis Horwood Ltd, 145–180; EP-A-O 576 970, EP-A-O 549 900, EP-A-O 522 581, EP-A-O 519 237, EP-A-O 468 537, EP-A-O 420 436, EP-A-O 416 815, EP-A-O 302 424.

These compounds are initially charged in an inert solvent which is preferably one or a mixture of aliphatic and/or aromatic hydrocarbons.

The hydrocarbons useful as a solvent preferably have boiling points between 50° and 150° C., in particular between 70°–120° C. Suitable hydrocarbons include substituted and unsubstituted aliphatic hydrocarbons, and substituted and unsubstituted aromatic hydrocarbons, having boiling points of 50°–150° C. Preferred solvents include hexane, heptane, octane, decane, toluene and xylene.

Trimethylaluminum (TMA) is metered into this mixture while stirring vigorously at room or elevated temperature.

Depending on the desired degree of substitution (monomethyl compounds, i.e., n is 1 in formula (1) or dimethyl compounds, i.e., n is 2 in formula (1)), the molar ratio of halogen-transition metal compound:TMA is from 1:1.1 to 1:2.4 and preferably about 1:1 to about 1:2. In the case of the dimethyl compounds, the excesses are not critical, but, with regard to process economy, should be kept as small as possible.

The mixture of halogen-transition metal compound and TMA is reacted with vigorous stirring at temperatures of 20°–120° C. preferably 70°–100° C. At these temperatures, reaction times of 0.5–1.5 hours are sufficient.

The reaction mixture is, after optionally cooling to room temperature, admixed with an alkali metal and/or alkaline earth metal fluoride, preferably NaF or KF. Preference is here given to the molar ratio of $F^-$ to TMA being about 1:1.

With reference to the reaction schemes depicted above, M' is an alkali metal or alkaline earth metal, and X' is fluoride.

For the quantitative formation of the methyl-transition metal compound, the reaction is advantageously carried out to completion for 0.5–1.5 hours at 70°–100° C.

The insoluble aluminum fluoride complexes formed are separated off by conventional methods such as decantation, centrifugation and/or filtration.

The filtrate, which contains the methyl-transition metal compounds in high purity and yield, can without further work-up processes be directly used in the polymerization of olefins.

If desired, the methyl-transition metal compounds can also be isolated by conventional methods.

This is to be illustrated by the following examples. All reactions were carried out with exclusion of moisture and of $O_2$ in an inert gas atmosphere.

EXAMPLES

Example 1 a) Reaction of indenyl$_2$ZrCl$_2$ with TMA/KF in toluene 20 g of indenyl$_2$ZrCl$_2$ (51 mmol) were initially charged in 250 ml of toluene and admixed with 7.35 g of trimethylaluminum (102 mmol) and the mixture was heated to 80° C.

After 30 minutes, 5.92 g of KF (102 mmol) were added and the mixture was refluxed for 1 hour.

The reaction solution was then filtered hot and the filtrate was cooled to –20° C.

14.2 g (79%) of indenyl$_2$ZrMe$_2$ was isolated by means of filtration.

$^1$H-NMR (CDCl$_3$): 7.5–7.4 (m, 4H, aromatic H); 7.15–7.05 (m, 4H, aromatic H); 6.08 (d, 4H, C$_5$H$_2$); 5.95 (t, 2H, C$_5$H); –1.15 (s, 6H, CH$_3$) Zr: found: 24.8% (calc.: 25.9%); Hydrolysis gas: CH$_4$: found: 127 standard ml/g (calc.: 127.4 standard ml/g)

b) Reaction of indenyl$_2$ZrCl$_2$ with KF/TMA in heptane

The procedure was similar to 1 a), but heptane was used in place of toluene. 14.75 g (83%) of clean product were obtained. Zr: found: 25.1% (calc.: 25.9%); Hydrolysis gas: CH$_4$: found: 127 standard ml/g (calc.: 127.4 standard ml/g) [1-H-NMR identical with that in 1 a)]

Example 2

Reaction of ethyleneindenyl$_2$ZrCl$_2$ with KF/TMA 19.2 g of rac-ethyleneindenyl$_2$ZrCl$_2$ (45.9 mmol) in 200 ml of heptane were initially charged and admixed with 7.35 g of trimethylaluminum (102 mmol).

After refluxing for ½ hour, 5.92 g of KF (102mmol) were added and the mixture was refluxed for a further 1 ½ hours.

After hot filtration, the filtrate was evaporated to 50 ml and cooled to –20° C.

15 g of pure ethyleneindenyl$_2$ZrMe$_2$ (86.5% of theory) was finally isolated by means of filtration. Zr: found: 23.5% (calc.: 24.2%); Hydrolysis gas: CH$_4$: found: 115 standard ml/g (calc.: 118.6 standard ml/g)

$^1$H-NMR (CDCl$_3$): 7.5–7.0 (m, 8H, C$_6$H$_4$); 6.55 (d, 2H, C$_5$H); 6.0 (d, 2H, C$_5$H); 3.4–3.1 (m, 4H, —CH$_2$CH$_2$—); –1.4 (s, 6H, CH$_3$).

Example 3

Reaction of Cp$_2$ZrCl$_2$ with KF/TMA 1.94 g of $Cp_2ZrCl_2$ (6.64 mmol) were suspended in 10 ml of heptane and admixed with 0.96 g of trimethylaluminum (13.8 mmol) and refluxed for ½ hour. After addition of 0.77 g of KF, the mixture was refluxed for a further 60 minutes.

Subsequently, $^1$H-NMR was able to detect only the desired compound $Cp_2ZrMe_2$ as metallocene in the solution.

$^1$H-NMR ($CDCl_3$): 6.1 (s, 10H, $C_5H_5$), –0.4 (s, 6H, $CH_3$)

Example 4

Reaction of n-butyl$Cp_2ZrCl_2$ with KF/TMA 1.94 g of n-butyl$Cp_2ZrCl_2$ (4.8 mmol) were added to 10 ml of heptane, admixed with 0.7 g of trimethylaluminum (9.6 mmol) and stirred for ½ hour at 80° C.

0.56 g of KF (9.6 mmol) was then added and again refluxed for 1 hour. $^1$H-NMR spectroscopy was then able to detect only the desired compound n-butyl$Cp_2ZrMe_2$ as metallocene in the solution.

Neither the starting material n-butyl$Cp_2ZrCl_2$ nor the intermediate stage n-butyl$Cp_2ZrCl(CH_3)$ were detectable.

$^1$H-NMR ($CDCl_3$): 5.95–5.9 (m, 4H, $C_5H_2$), 5.83–5.78 (m, 4H, $C_5H_2$) 2.45 (t, 4H, —$CH_2$—); 1.6–1.25 (m, 8H, —$CH_2$—$CH_2$); 0.95 (t, 6H, $CH_3$); –0.5 (s, 6H, $CH_3$).

Example 5

Reaction of 1,3-butylmethyl$Cp_2ZrCl_2$

The procedure was similar to that in Example 4, but using 2.1 g (4.8 mmol) of 1,3-butylmethyl$Cp_2ZrCl_2$ instead of n-butyl$Cp_2ZrCl_2$.

Again, only the desired 1,3-n-butylmethyl$Cp_2$ $ZrMe_2$ was able to be detected as metallocene compound.

$^1$H-NMR ($CDCl_3$): 5.78 (t, 2H, $C_5H$) 5.52 (d, 4H, $C_5H_2$); 2.4–2.15 (m, 4H, —$CH_2$—); 2.05 (s, 6H, $CH_3$); 1.6–1.3 (m, 8H, —$CH_2CH_2$—); 0.9 (t, 6H, $CH_3$); –0.53 (s, 6H, $CH_3$).

Example 6

Reaction of $Me_2Si[(^tBuN)(Me_4Cp)]TiCl_2$ with KF/TMA 2.38 g (6.4 mmol) of $Me_2Si[(Me_4Cp)(N^tBu)]TiCl_2$ were initially charged in 10 ml of heptane and admixed at room temperature with 1 g of trimethylaluminum (13.8 mmol).

The mixture was refluxed for 30 minutes and then admixed with 0.84 g of KF (13.8 mmol) and again refluxed for 30 minutes.

Subsequently, $^1$H-NMR was able to detect only the compound $Me_2Si[(Me_4Cp)(N^tBu)]TiMe_2$ in the reaction solution.

$^1$H-NMR ($CDCl_3$): 2.18 (s, 6H, $Me_2Cp$); 1.92 (s, 6H, MeCp); 1.58 (s, 9H, t-butylN); 0.48 (s, 6H, $(H_2C)_2Si$); 0.18 (s, 6H, $(H_3C)_2Ti$).

Example 7

Reaction of n-butyl$Cp_2HfCl_2$ with KF/TMA 2.21 g of bis(n-butylcyclopentadienyl)hafnium dichloride (4.49 mmol) were initially charged in 30 ml of heptane and admixed at room temperature with 1.76 ml of trimethylaluminum. The mixture was subsequently stirred for 30 minutes at 90° C.

1.04 g of potassium fluoride (17.98 mmol) were then added and the mixture was stirred for a further 30 minutes at 90° C.

$^1$H-NMR spectroscopy showed only the desired product bis(n-butylCp)$HfMe_2$ and no longer any starting material.

$^1$H-NMR ($CDCl_3$): 5.85 (m, 4H, $H_2Cp$); 5.75 (m, 4H, $H_2Cp$); 2.45 (t, 4H, —$CH_2$—); 1.65–1.2 (m, 8H, —$CH_2CH_2$—); 0.95 (t, 6H, —$CH_3$); –0.62 (s, 6H, $H_3C$—Ti).

Example 8

Attempt at the reaction of indenyl$_2ZrCl_2$ with LiCl/TMA 25 g of indenyl$_2ZrCl_2$ (64 mmol) were initially charged in 200 ml of heptane, admixed with 25 ml of trimethylaluminum (255 mmol) and refluxed for 1 hour.

10.81 g of LiCl (255 mmol) were then added and the mixture was again refluxed for 1 hour.

$^1$H-NMR was able to detect no formation of the desired dimethyl derivative.

Example 9

Attempt at the reaction of indenyl$_2ZrCl_2$ with $ZnCl_2$ 2.7 g of indenyl$_2ZrCl_2$ (7.5 mmol) were initially charged in 30 ml of heptane, admixed with 2.7 ml of trimethylaluminum (28 mmol) and refluxed for 1 hour.

4.24 g of zinc chloride (28 mmol) were then added and the mixture was again refluxed for 1 hour.

No formation of the desired dimethyl derivative was able to be observed by means of $^1$H-NMR.

Example 10

Attempt at the reaction of indenyl$_2ZrCl_2$ with KCl/TMA 2.92 indenyl$_2ZrCl_2$ (7.5 mmol) were initially charged in 30 ml of heptane together with 2.92 g of trimethylaluminum (30 mmol) and refluxed for 1 hour.

2.22 g of KCl (30 mmol) were then added, and the mixture was refluxed for a further 2 hours.

$^1$H-MNR was able to detect no formation of indenyl$_2ZrMe_2$.

Example 11

Reaction of indenyl$_2ZrCl_2$ with NaF/TMA 40 g of indenyl$_2ZrCl_2$ (102 mmol) were initially charged in 400 ml of heptane and admixed with 40 ml of trimethylaluminum (408 mmol). The mixture was refluxed for 1 hour.

17.13 g of NaF (408 mmol) were then added, and the mixture was refluxed for a further 2 hours.

The reaction solution was filtered hot and cooled to –20° C.

9.91 g (27.5% or, theory) of pure indenyl$_2ZrCl(CH_3)$ were able to be isolated.

$^1$H-NMR: 7.6–7.15 (m, 8H, $C_6H_4$); 6.2–6.05 (m, 6H, $C_5H_3$); –0.55 (s, 6H, $CH_3$).

Example 12

Reaction of indenyl$_2ZrCl_2$ with KF/TMA (1:1)

50 g (128 mmol) of indenyl$_2ZrCl_2$ were initially charged in 500 ml of heptane and admixed at room temperature with 12.6 ml (128 mmol) of trimethylaluminum. The mixture was refluxed for 1 hour.

7.95 g (128 mmol) of KF were then added, and the mixture was refluxed for a further 2 hours.

After hot filtration to remove the insoluble salts, the filtrate was cooled to –20° C.

31.8 g (71% of theory) of pure indenyl$_2$ZrCl(CH$_3$) were able to be isolated by means of filtration.

$^1$H-NMR (identical with that in Example 11).

Comparative Examples a) Reaction of Me$_2$Si[(Me$_4$Cp)(N$^t$Bu)]TiCl$_2$ with TMA without addition of KF.

2.4 g (6.5 mmol) of Me$_2$Si[(Me$_4$Cp)(N$^t$Bu)]TiCl$_2$ were initially charged in 10 ml of heptane and admixed with 1.92 g of trimethylaluminum. The mixture was then refluxed for 1 hour.

Subsequently, $^1$H-NMR was able to detect the monomethylated compound in small amounts (14%). However, the solution comprised 86% of the starting material, the corresponding titanium dichloride complex. (However, if 1.55 g of KF were then added and the mixture was allowed to react for a further 1 hour at 80° C., quantitative formation of the dimethyltitanocene resulted.)

b) Separate reaction of KF and trimethylaluminum prior to use for the methylation of Me$_2$Si[(Me$_4$Cp)(N$^t$Bu)]TiCl$_2$.

0.46 g of KF (8 mmol) and 0.8 ml (8 mmol) of trimethylaluminum were stirred in 10 ml of heptane for ½ hour at 90° C. 1.48 g of Me$_2$Si[(Me$_4$Cp)(N$^t$Bu)]TiCl$_2$ were then added at room temperature, and the mixture was stirred for a further 3 hours at 80° C.

$^1$H-NMR was able to detect, besides the starting compound (82%), only the monomethylated compound (18%).

c) Addition of KF to Me$_2$Si[(Me$_4$Cp)(N$^t$Bu)]TiCl$_2$.

0.96 g of KF (16.5 mmol) and 2.04 g of the titanium dichloride compound were initially charged in 10 ml of heptane and stirred for 1 hour at 80° C.

No reaction (replacement of Cl by F) could be detected.

What is claimed is:

1. A process for preparing a methyl-transition metal compound of the general formula (1)

$$(Q)_m(CpR_a)(Cp'R'_a)M(CH_3)_nX_{2-n} \qquad (1)$$

wherein

Cp is a cyclopentadienyl, an indenyl or a fluorenyl radical;

R and R' are each independently alkoxy, alkylamino, dialkylamino, aryl-alkyl, aryloxy-alkyl or phosphine; $0 \leq a \leq 5$ and $0 \leq a' \leq 5$;

Cp' is one of the groups Cp or when a' is 1 Cp'R' can be NR' wherein R' is an alkyl or aryl radical; and Q is a single-membered or multi-membered bridge $$(R^1-Z-R^2)_b$$

between Cp and Cp', wherein R$^1$ and R$^2$ are identical or different and are a hydrogen atom, a C$_1$–C$_{10}$-alkyl group or a C$_6$–C$_{10}$-aryl group; Z is carbon, silicon or germanium; and b is 1, 2, or 3;

M is a transition metal of the groups III to VI;

X is halogen;

n can be 1 or 2; and m can be 0 or 1;

comprising reacting one or more halogen-transition metal compounds of formula (2)

$$(Q)_m(CpR_a)(Cp'R'_a)MX_2 \qquad (2)$$

with trimethylaluminum in a hydrocarbon solvent, then admixing into the reaction solution one or more fluorides selected from the group consisting of alkali metal fluorides and alkaline earth metal fluorides whereby one or more complexes comprising aluminum and fluoride are formed, and subsequently separating the one or more complexes from said reaction solution.

2. A process according to claim 1, wherein the reaction is carried out at a temperature of 20°–120° C.

3. A process according to claim 1, wherein said solvent in which the reaction is carried out is selected from the group consisting of substituted and unsubstituted aliphatic hydrocarbons and substituted and unsubstituted aromatic hydrocarbons having boiling points between 50°–150° C., and mixtures thereof.

4. A process according to claim 1, wherein said fluoride is NaF or KF.

5. A process according to claim 1, wherein the molar ratio of said one or more halogen-transition metal compounds:trimethylaluminum:fluoride is 1:1:1 when n is 1 in formula (1), and said ratio is 1:2:2 when n is 2 in formula (1).

6. A process according to claim 1 wherein M is Ti, Zr or Hf.

7. A process according to claim 1 wherein X is Cl or Br.

* * * * *

UNITED STATES PATENT AND TRADEMARK OFFICE
CERTIFICATE OF CORRECTION

PATENT NO. : 5,523,435
DATED : June 4, 1996
INVENTOR(S) : Richard Lisowsky, et al.

It is certified that error appears in the above-indentified patent and that said Letters Patent is hereby corrected as shown below:

Column 2, line 46: before "can be 1 or 2;"

insert -- n --

Column 2, line 47: before "can be 0 or 1."

insert -- m --

Signed and Sealed this

Ninth Day of September, 1997

*Attest:*

BRUCE LEHMAN

*Attesting Officer*     Commissioner of Patents and Trademarks